United States Patent [19]
Dumler et al.

[11] Patent Number: 5,955,359
[45] Date of Patent: Sep. 21, 1999

[54] **METHOD OF GROWING GRANULOCYTIC EHRLICHIAE OF THE *EHRLICHIA PHAGOCYTOPHILA* GENOGROUP IN PROMYELOCYTIC LEUKEMIA CELL CULTURE, AND PREPARING ANTIGENS AND VACCINES OF SAID GRANULOCYTIC EHRLICHIAE**

[75] Inventors: J. Stephen Dumler, Ellicott City, Md.; John Madigan, Woodland, Calif.; Jesse Goodman, Minneapolis, Minn.

[73] Assignees: University of Maryland at Baltimore, Baltimore, Md.; The Regents of the University of California, Oakland, Calif.; Regents of the University of Minnesota, Minneapolis, Minn.

[21] Appl. No.: 08/788,711

[22] Filed: Jan. 23, 1997

Related U.S. Application Data

[63] Continuation-in-part of application No. 08/519,283, Aug. 25, 1995.

[51] Int. Cl.[6] .................................................. C12N 1/00
[52] U.S. Cl. ......................... 435/348; 435/243; 435/260; 435/374; 435/253.6; 435/248; 435/395; 424/265.1
[58] Field of Search ................................ 435/240.1, 243, 435/260, 348, 374, 253.6, 395, 248; 424/265.1

[56] References Cited

U.S. PATENT DOCUMENTS 5,192,679  3/1993  Dawson et al. .

OTHER PUBLICATIONS

Collins et al, *Nature*, 270:347–349 (1977).
Ristic et al, Tribe II: Ehrlichieae Philip 1957, 948[AL], *Bergey's Manual of Systematic Bateriology*, 1:704–711, Eds Noel R. Krieg and John G. Holt, Williams and Wilkens Balto. (1984).
Rikihisa, "The Tribe Ehrlichieae and Ehrlichial Diseases", *Clin. Microbiol. Rev.*, 4:286–308 (1991).
Brodie et al, "Some Aspects of Tick–Borne Diseases of British Sheep", *The Veterinary Record*, 118:415–418 (1986).
Rodgers et al, "A Serological Survey of *Ehrlichia canis, Ehrlichia equi, Rickettsia rickettsii,* and *Borrelia burgdorferi* in Dogs in Oklahoma", *J. Vet. Diagn. Invest.*, 1:154–159 (1986).
"Human Granulocytic Ehrlichiosis", *Morsidity and Mortality Weekly Report*, 44(32):593–595 (1995).
Macleod et al, "Studies in Tick–Borne Fever of Sheep", *Parasitology*, 25:273–283 (1933).
Bakken et al, "Human Granulocytic Ehrlichiosis in the Upper Midwest United States", *JAMA*, 272(3):212–218 (1994).
Winjum et al, "In Vitro Proliferation of a Canine Granulocytic Ehrlichia", *Vet. Microbiology*, 34:355–362 (1993).
Munderloh et al, "Formulation of Medium for Tick Cell Culture", *Experimental and Applied Acarology*, 7:219–229 (1989).
Sells et al, "Ultrastructural Observations on *Ehrlichia equi* Organisms in Equine Granulocytes", *Infection and Immunity*, 13(1):273–280 (1976).
Chen et al, "Identification of a Granulocytotropic Ehrlichia Species as the Etiologic Agent of Human Disease", *J. of Clin. Microbiology*, 32(3):589–595 (1994).
Dumler et al, "Serologic Cross–Reactions Among *Ehrlichia equi*, *Ehrlichia phagocytophila*, and Human Granulocytic Ehrlichia", *J. of Clin. Microbiology*, 33(5):1098–1103 (1995).
Wyoski et al, "Spermatogenesis, Chromosomes and Sex Determination of Four Rhipicephalus Species (Acari: Ixodidae) from East Africa", *Genetica*, 48(3):233–238 (1978).
Sitbon et al, "Hemolytic Anemia and Erythroleukemia, Two Distinct Pathogenic Effects of Friend MuLV: Mapping of the Effects of Different Regions of the Viral Genome", *Cell*, 47:851–859 (1986).
Oliver et al, "Conspecificity of the Ticks *Ixodes scapularis* and *I. dammini* (Acari: Ixodidae)", *J. Med. Entomol.*, 30(1):54–63 (1993).
Madigan et al, "Seroepidemiologic Survey of Antibodies to *Ehrlichia equi* in horses of Northern California", *Javma*, 196(12):1962–1964 (1990).
Kurtti et al, "The Effects of 20–Hydroxyecdysone and Juvenile Hormone III on Tick Cells", *J. Parasitol.*, 69(6):1072–1078 (1983).
Goodman et al, "Direct Cultivation of the Causative Agent of Human Granulocytic Ehrlichiosis", *New England Journal of Medicine*, 334:209–15 (Jan. 25, 1996).
Dumler et al, "In Vitro Cultivation of the Agents of Human and Equine Granulocytic Ehrlichiosis", *Abstracts of the Twelfth Sesqui–Annual Meeting of the American Society for Rickettsiology and Rickettsial Diseases*, Pacific Grove, Ca. (Mar. 10–13, 1996).
Dumler et al, "Diagnosis of Granulocytic Ehrlichiosis by Cell Culture", *Abstracts of the 96th General Meeting of the American Society for Microbiology*, New Orleans, La. (May 19–23, 1996).

*Primary Examiner*—James C. Housel
*Assistant Examiner*—Jennifer Graser
*Attorney, Agent, or Firm*—Sughrue, Mion, Zinn, Macpeak & Seas, PLLC

[57] ABSTRACT

Methods for the in vitro cultivation, propagation, and production of antigens of *Ehrlichia phagocytophila* genogroup granulocytic Ehrlichia species, including *Ehrlichia equi* and the agent of human granulocytic ehrlichiosis in promyelocytic leukemia cell cultures, such as HL60 and KG-1 cell lines.

5 Claims, No Drawings

METHOD OF GROWING GRANULOCYTIC EHRLICHIAE OF THE *EHRLICHIA PHAGOCYTOPHILA* GENOGROUP IN PROMYELOCYTIC LEUKEMIA CELL CULTURE, AND PREPARING ANTIGENS AND VACCINES OF SAID GRANULOCYTIC EHRLICHIAE

CROSS-REFERENCE TO RELATED APPLICATIONS

This is a Continuation-in-Part of U.S. patent application Ser. No. 08/519,283, filed Aug. 25, 1995, which is incorporated by reference herein in its entirety.

The work described herein was supported in part with funds from the Minnesota Agricultural Experiment Station (Project 377-3457), a Special Research Initiative Support Award from the University of Maryland School of Medicine, and Equine Research Laboratory Grant No. 95-01 from the University of California, Davis.

FIELD OF THE INVENTION

The present invention relates to methods for the in vitro cultivation of granulocytic Ehrlichia species of the *Ehrlichia phagocytophila* genogroup in promyelocytic leukemia cells, such as HL60 and KG-1 cells.

BACKGROUND OF THE INVENTION

Ehrlichiae are obligate intracellular bacteria that predominantly infect bone marrow-derived cells in their mammalian hosts. Those species, for which a biological vector is known, are transmitted by ticks. Typically, Ehrlichiae are contained within a membrane-lined vacuole of their host cell.

Ehrlichiae species were initially characterized on the basis of host cell type, host species, and serologic cross-reactivity. Ehrlichiae may be divided into three phylogenetically distinct groups on the basis of nucleotide sequences of the 16S ribosomal RNA genes in each species and strong serologic cross-reactions. Each group is denoted by the historical precedent for the genetic group.

The *Ehrlichia canis* group includes 3 species known to infect predominantly monocytes and macrophages, and a single species known to infect canine granulocytes. *Ehrlichia canis*, the type species, *E. chaffeensis*, and *E. muris* infect mononuclear phagocytes of dogs, humans, and mice, respectively, while *E. ewingii* infects canine granulocytes (Ristic et al, In: *Bergey's manual of Systematic Bacteriology*, 1(9):1957 (1984)).

The second genetic group, the *E. sennetsu* group, includes *E. sennetsu* and *E. risticii*. They are monocytic Ehrlichiae that are agents of human Sennetsu fever of Japan and Potomac horse fever (equine monocytic ehrlichiosis) of horses worldwide.

The third group, the *E. phagocytophila* (Ep) genogroup, includes the granulocytic Ehrlichiae, *E. equi*, the agent of equine granulocytic ehrlichiosis (EGE) of horses, and an agent of canine granulocytic ehrlichiosis in the US, South America, and Europe; *E. phagocytophila*, the agent of tick-borne fever of ruminants in Europe; an as yet unnamed Ehrlichiae that is the causative agent of human granulocytic ehrlichiosis (HGE) in the United States and Europe; and more distantly, *E. platys*, a thrombocytic Ehrlichiae that causes mild cyclical thrombocytopenia in dogs.

Emerging genetic and antigenic data indicates that the members of the *E. phagocytophila* genogroup are very closely related or identical species (Chen et al, *J. Clin. Microbiol.*, 32:589 (1994)). In humans, HGE was first recognized in 1990 (Chen et al, supra), and is considered an emerging disease of increasing clinical significance.

None of the granulocytic Ehrlichiae have been continuously propagated in vitro. This has continuously hampered the development of diagnostic tools for these infections, and investigation of the diseases and causative agents.

The clinical presentation of granulocytic ehrlichioses in man and animals are nonspecific and include fever, headache, rigors and malaise in humans, and fever, depression, and sometimes lameness in animals (Rikihisa, *Clin. Microbiol. Rev.*, 4:286 (1991)). Ehrlichiae infections have dramatic effects on the hematologic and hepatic systems, and most infected humans and animal species develop leukopenia, thrombocytopenia, anemia, and evidence of mild hepatic injury. The appearance of membrane-bound vacuoles containing the pathogens within circulating leukocytes is suggestive of the diagnosis. However, human patients and some animals infrequently present with infected leukocytes in the peripheral blood.

Tetracycline antibiotics are the drug of choice for treatment of all ehrlichioses, and most human patients respond with a dramatic defervescence after therapy (Dumler et al, *Clin. Infect. Dis.*, 20:1102 (1995)). In most cases, prevention of ehrlichioses focuses on vector control and prophylaxis using tetracyclines. The only agent for which a vaccine exists is *E. risticii*, which is cultivatable in vitro (Rikihisa, supra).

The exact economic toll extracted by the Ep group of Ehrlichiae is not known. In Great Britain, it is estimated that 2% of the entire goat population dies each year from secondary infections that occur only after *E. phagocytophila* infections (Brodie et al, *Vet. Rec.*, 118:415 (1986)). In the United States, equine and canine infections with *E. equi* have been infrequently documented because of the lack of suitable diagnostic tools and nonspecific presentation of the illness. However, with the recent recognition that the agent of HGE is nearly identical genetically (Chen et al, supra), and antigenically (Dumler, *J. Clin. Microbiol.*, 33:1098 (1995)), biologically with *E. equi*, and is capable of causing severe and fatal human infection, there has been an increased awareness of the prevalence of equine and canine infections. serologic evidence of *E. equi* infection in some regions of California has been identified in up to 50% of the horses residing in those regions (Madigan et al, *J. Am. Vet. Med. Assoc.*, 196:1962 (1990)). Similarly, nearly 20% of animals tested in a serosurvey of ill dogs in Oklahoma had evidence of *E. equi* infection (Rodgers et al, *J. Vet. Diagn. Invest.*, 1:154 (1989)). Since the first identified case of HGE in 1990, there has been a logarithmic increase in the number of diagnoses of that human infection, especially since modern diagnostic methods have become available through specialized academic research facilities and some commercial laboratories. To date, approximately 115 cases of HGE have been recognized in the United States (Wormser et al, *MMWR*, 44:593 (1995)). Initial studies suggest that approximately 10% of human patients with Lyme disease may have been infected with the agent of HGE. Given the nearly 10,000 cases of Lyme disease reported annually in the United States, one would speculate that perhaps 1,000 of these patients may have also acquired undiagnosed HGE, in addition to those patients with HGE not accompanied by Lyme disease.

*Ehrlichia phagocytophila* and *E. equi* are transmissible through the bite of *Ixodes ricinus* (MacLeod et al, *Parasitology*, 25:273 (1933)) and *I. pacificus* ticks, respectively. Mounting evidence has implicated *Ixodes scapularis*

(*dammini*) ticks as the vector responsible for transmitting the agent of HGE in the United States (Bakken et al, *JAMA*, 272:212 (1994)). It is assumed that larval ticks acquire the pathogen from a reservoir host, probably wild rodents, and that subsequent developmental stages, i.e., the nymphs and adults, transmit the Ehrlichiae during their blood meal.

Specific diagnosis of HGE, EGE, and tick-borne fever is accomplished by serology (Bakken et al, supra; Dumler, supra; and Madigan, supra), utilizing antigen prepared from infected animals. Diagnosis in animals is often suspected when typical intracytoplasmic inclusions are present in the peripheral blood leukocytes of febrile animals. In contrast, Ehrlichiae inclusions are variably present in the peripheral blood of humans who nevertheless may be very ill. As for other rickettsiae infections, the single most important determinant of clinical outcome is early diagnosis and early therapy with specific antimicrobial agents. If these patients are not treated promptly, the disease may quickly proceed to severe disease or a fatal outcome. Fatalities appear to be related to the development of secondary opportunistic infections that occur after the Ehrlichiae infection. Treatment with tetracycline antibiotics leads to a rapid therapeutic response (Bakken, supra).

Attempts to propagate *E. equi* and *E. phagocytophila* in vitro in primary neutrophils harvested from the peripheral blood of infected animals have yielded short term (48 to 72 hr) increases in the percentage of infected cells (Winjum et al, *Vet. Microbiol.*, 34:355 (1993)). However, supplementation of the cultures with additional primary, uninfected neutrophils is unable to provide a continuous propagation system. This finding implies that mature neutrophils are probably not competent to become infected, but that new cells become infected as immature cells, probably in the bone marrow. A search for a susceptible mammalian cell line has been fruitless so far, and other cell lines known to support the growth of other Ehrlichiae species, such as DH-82, P388D$_1$, U937, HEL, and Vero cells, do not support the growth of *E. equi* when co-cultivated with primary clinical samples.

Even more enigmatic is the biology of granulocytic Ehrlichiae in their tick vector. There is evidence, based on indirect immunofluorescent assays, that the organisms invade hemocytes of the tick, but other target tissues, if any, are unknown. By analogy with *Anaplasma marginale*, a related pathogen of cattle, it is expected that in the vector tick, a number of tissue types are invaded by *E. equi* and its relatives. Particularly, one can expect that the salivary glands of ticks should be invaded, as they would provide the rickettsiae with an obvious route of transmission to the mammal or to man. It is believed that culture systems for the production of the Ep group Ehrlichiae stages found in the mammal and in the vector would be valuable tools to elucidate the biology of these granulocytic Ehrlichiae in mammals, as well as in ticks, and would facilitate the development of appropriate diagnostic tools for HGE, and potentially an effective vaccine.

Because of the increasing prevalence and incidence of HGE and granulocytic ehrlichioses of horses and dogs, there is a need to develop reliable diagnostic tools that utilize antigen produced in vitro instead of in animals, such as horses. This capability will provide a more consistent, reproducible antigen for diagnosis, and will offer the ability for large scale production of both the mammalian stages and the vector stages in vitro.

SUMMARY OF THE INVENTION

This invention is directed to methods of growing or culturing Ep group granulocytic Ehrlichiae, such as *Ehrlichia equi* and the human granulocytic Ehrlichia, in promyelocytic leukemia cell cultures, such as HL60 and KG-1 cell cultures.

A method of the invention provides for growth of Ep group Ehrlichiae, such as *E. equi* and the human granulocytic Ehrlichia, in promyelocytic cell lines. Ehrlichia equi-infected blood containing cells, such as *E. equi-* or human granulocytic Ehrlichia-infected peripheral blood neutrophils, are incubated with cells of a promyelocytic leukemia cell line, such as human HL60 or KG-1 cells. Preferably, the cultures are incubated in medium with enhanced $CO_2$ of about 5% at a temperature of 37° C. The method is useful for preparation of Ep group Ehrlichiae antigens, such as *E. equi* or human granulocytic Ehrlichia antigens, that react with antibodies made by mammals and humans after infection by Ep group Ehrlichiae. Thus, the method is useful to prepare antigens or nucleic acids for diagnostic or vaccine applications.

DETAILED DESCRIPTION OF THE INVENTION

This invention includes methods to culture the obligate intracellular Ep group granulocytic Ehrlichiae species from peripheral blood in cultures of promyelocytic leukemia cells, e.g., HL60 and KG-1 human cell lines, which cell lines were deposited with the ATCC in 1982 (ATCC No. CCL 240 and ATCC No. CCL 246). Any other promyelocytic leukemia cell line can be used in the present invention, e.g., K-562 (ATCC No. CCL 243), HEL-92.1.7 (ATCC NO. TIB 180), ML-1 (Kastan et al, *Cancer Res.*, 51:6304–6311 (1991), X-CGD PLB-985 (Ding et al, *Blood*, 88:1834–1840 (1996), LAMA-84 (Blom et al, *Scand. J. Immunol.*, 44:54–61 (1996), M-NF5-60 (ATCC No. CRL 1838), WEHI-3 (ATCC No. TIB 68), and M1 (ATCC No. TIB 192).

Ep group Ehrlichiae have not previously been successfully propagated in continuous cell culture, yet, these bacteria are causes of emerging zoonotic infections of domestic animals and humans. A method of growing Ep group granulocytic Ehrlichiae in vitro is useful to prepare diagnostic reagents, antigen preparations, and vaccine preparations. The method of this invention is useful to grow and/or culture Ep group Ehrlichiae on a large scale, resulting in production of Ehrlichiae containing products at a high yield, and much reduced cost. In addition, large scale in vitro culture eliminates the need to maintain and/or sacrifice *E. equi*-infected horses that can cost in excess of $700.00 for a single horse.

An in vitro culture method in promyelocyte cell lines, such as HL60 and KG-1, is advantageous because Ep group Ehrlichiae can be obtained that are highly purified and that may express mammalian infection-stage specific ehrlichial antigens or RNA. These preparations might be advantageous in stimulating a protective immune response, detecting antibodies produced in mammalian and human infections with Ep genogroup Ehrlichiae, producing nucleic acid-based diagnostic reagents for infections by Ep genogroup Ehrlichiae, or in producing mammalian stage-specific recombinant antigens or proteins from Ep genogroup ehrlichial nucleic acids.

A. Ep Group Granulocytic Ehrlichiae: *E. equi*, *E. phagocytophila*, and the HGE Agent Ehrlichiae include species that are tick transmitted disease agents. *Ehrlichia equi*, the causative agent of EGE, is tick transmitted, as is *E. phagocytophila*, the causative agent of tick-borne fever of ruminants in Europe. These Ehrlichiae are very closely related to or identical to the newly identified, probably tick-transmitted agent of HGE, which is known to cause a potentially fatal disease in humans. Because of the nearly identical 16S ribosomal RNA gene sequence, strong antigenic similarities, and biological identity, *E. equi, E. phagocytophila,* and the agent of HGE, are probably variants of a single species.

In man and animals, these Ehrlichiae infect granulocytic leukocytes, and cause severe febrile diseases that may be associated with decreased host resistance to opportunistic infections. Each of these Ep group granulocytic Ehrlichiae is known or suspected to be transmitted by *Ixodes ricinus* complex (including *I. ricinus* (sheep ticks) in Europe, *I. pacificus* (western black-legged ticks) in California, and *I. scapularis* (deer ticks or eastern black-legged ticks) in the midwestern and eastern United States) ticks. Only those forms that comprise the morulae (the intracytoplasmic clusters of Ehrlichiae organisms) found in mammalian hosts have been investigated and described in some detail. In the neutrophil, Ehrlichiae of the Ep group are always contained within a vacuole of the host cell. Individual Ehrlichiae are described as coccoid to cocco-bacillary in shape, but may be highly pleomorphic. Up to about 20 organisms occupy one morulae in a mammalian leukocyte. The forms that are resident in the vector are not known, and have not been described. Therefore, growing Ep group granulocytic Ehrlichiae in *Ixodes scapularis* cell culture offers the opportunity to analyze and utilize antigens uniquely associated with the vector. Conversely, the availability of the exact same agent in a human cell line provides the chance to study the molecular and cellular interactions of the organism with the human host cells in vitro, and to contrast the two life stages, arthropod and vertebrate, for this organism.

*Ehrlichia equi* or the human granulocytic Ehrlichia obtained from infected horses or the human granulocytic Ehrlichia obtained from human patients with human granulocytic ehrlichiosis can be grown in promyelocyte cell cultures. In a method of the invention, Ep group granulocytic Ehrlichiae, such as *E. equi* or the human granulocytic Ehrlichia, are incubated with promyelocyte cell line cultures, preferably HL60 or KG-1 cell cultures. The *E. equi* and human granulocytic Ehrlichia inoculum can be obtained from horses after experimental inoculation with thawed, *E. equi*- or human granulocytic Ehrlichia-infected blood from an acutely infected horse, followed by venipuncture and removal of fresh, infected blood at a time when Ehrlichiae are visible in the peripheral blood leukocytes of the ill, infected horse. Alternately, the human granulocytic Ehrlichia inoculum can be obtained from human patients during the acute phase of human granulocytic ehrlichiosis at a time when typical Ehrlichia morulae are detected within leukocytes in the peripheral blood of the infected patient. The organisms found in the neutrophils are always contained within a membrane bound vacuole up to about 3 to 5 $\mu$m in diameter. The individual organisms are small, highly pleomorphic, and approximately 0.5 $\mu$m in size. With Romanowsky stains, such as Giemsa or LeukoStat, Ehrlichiae species and the morulae appear bluish-purple. By electron microscopy their electron density is similar to that of the host cytoplasm, but some morulae may contain smaller, dense forms.

*Ehrlichia equi* and human granulocytic Ehrlichiae agents can be cultured in promyelocytic leukemia cells, such as HL60 or KG-1 cells. In a method of the invention, Ep group granulocytic Ehrlichiae, such as *E. equi* or the human granulocytic Ehrlichia agent, in acute phase blood samples of naturally infected humans or animals or experimentally-infected animals such as horses, are incubated with log phase growth of promyelocytic leukemia cells, such as HL60 or KG-1 cells. For example, log phase growth HL60 or KG-1 cells are centrifuged and resuspended in tissue culture medium at a concentration of about $3.0\times10^6$ cell per ml. The preferred culture conditions include RPMI 1640 medium supplemented with about 10% (v/v) fetal bovine serum (heat-inactivated), about 2.0 mM L-glutamine, and in an atmosphere of 5% $CO_2$ at about 37° C. The co-cultivated cells are maintained in suspension cultures and are examined periodically, preferably weekly, by Romanowsky staining or immunofluorescence, for the presence of typical Ep genogroup Ehrlichia species morulae and antigens indicative of infection. Infected cells may contain single morulae typical in appearance, as seen in the peripheral blood neutrophils of patients with human granulocytic ehrlichiosis, and horses or dogs with *E. equi* granulocytic ehrlichiosis. With progressive time, an increasing percentage of cells become infected, and may contain multiple morulae, providing an in vitro method to obtain substantial quantities of Ep group Ehrlichiae propagated within mammalian (human) cells.

Growth and development of *E. equi* or the human granulocytic Ehrlichia agent in, e.g., HL60 or KG-1 cells can be detected by several methods. One method is to prepare cell spreads using a cytocentrifuge and to stain the cells with a Romanowsky stain. Infected cells can then be detected by the presence of Ehrlichiae inclusions in the cytoplasm. The inclusions seen in HL60 and KG-1 cells are similar to those seen in vivo in the neutrophilic granulocytes of humans, dogs and horses. Inclusions in heavily infected cells can completely fill the cytoplasm, and cause the cell to distend and rupture.

Alternatively, growth can be detected by immunocytological methods using specific *E. equi, E. phagocytophila,* or HGE agent antibodies in indirect fluorescent antibody methods and indirect immunoenzymatic methods.

*Ehrlichia equi* and human granulocytic Ehrlichia agent infection in vitro can also be detected by PCR using primers designed specifically to amplify only Ep group DNA. PCR can be conducted on isolated whole *E. equi*- or HGE agent infected cell culture DNA. Primers can be designed based upon the DNA sequence of the 16S ribosomal RNA gene in regions conserved among *E. equi, E. phagocytophila,* and the HGE agent. Primers are typically complementary to and/or hybridize to a 5' region and a 3' region of the nucleic acid sequence. Primers preferably have at least 15 nucleotides that are complementary to the nucleic acid sequence. Primers are preferably about 15 to 50 nucleotides long and can be prepared by automated synthesis.

The preferred primers amplify a 919 base pair fragment of the Ep group 16S ribosomal RNA gene and have the following sequences (Chen et al, supra): ge9f 5'-AACGGATTATTCTTTATAGCTTGCT-3' (SEQ ID NO:1) ge10r 5'-GGAGATTAGATCCTTCTTAACGGAA-3' (SEQ ID NO:2); or a 928 base pair fragment of the Ep group 16S ribosomal RNA gene and have the following sequences: EE3 5'-GTCGAACGGATTATTCTTTATAGCTTGC-3' (SEQ ID NO:3), EE4 5'-CCCTTCCGTTAAGAAGGATCTAATCTCC-3' (SEQ ID NO:4), PCR can be conducted as described in below.

The invention also includes promyelocytic leukemia cells, such as HL60 and KG-1 cells, infected with *E. equi* or the human granulocytic Ehrlichia agent. The infected cell cultures are useful as diagnostic tools for assays including ELISA, indirect fluorescent antibody tests, latex agglutination tests, complement fixation tests, and immunoblot tests. For immunofluorescence, it is preferred that 100 to 1000 cells be present on a slide with about 50% to 100%, and no less than 25% of cells infected.

The ability to grow infected mammalian cells on a large scale can provide for a enhancement in yield at a lower cost. An infected horse yields about 2.0 l of infected blood containing about $1.2 \times 10^6$ infected granulocytes per l. An infected horse costs approximately $700.00 to initiate infection, and to maintain the animal during the course of infection and convalescence. The animal can only be infected once, and new horses must continually be available. Moreover, biological variation among animals yields varied, and unpredictable levels of ehrlichemia and lack of reproducibility in *E. equi* and HGE agent production. Thus, the promyelocytic leukemia cells allow for reproducible, high quality, low cost production of Ehrlichia species for antigen, nucleic acid, and vaccine preparation.

Vaccine preparations can include whole microorganisms, antigen preparations, subunit vaccines, and/or nucleic acid vaccines. The vaccines can be heat-killed or live attenuated microorganisms. Vaccine formulations can be prepared in accordance with methods standard in the art.

Preferably, heat-killed vaccines and antigen preparations of Ep group granulocytic Ehrlichiae are made from Ep group granulocytic Ehrlichia species passaged in cell culture that retain infectivity for horses. *E. equi* passaged in tick cells at 3 passages retains infectivity for horses.

Preferably, the vaccine and antigen preparations are essentially free of horse antigens and/or other pathogens. Vaccine and antigen preparations from infected horses can be contaminated with horse antigens that can result in a formation of an immune response to the horse antigens. This immune response to horse antigens can cause adverse immunological responses in vaccinees. Contamination of horse blood with other pathogens may also occur since large amounts of blood are necessary to prepare vaccines and/or antigen preparations.

In contrast, Ep group granulocytic Ehrlichiae grown in cell culture can be produced on a large scale with little or no contamination with horse antigens or other equine pathogens. Electron micrographs of infected cultures indicate that contamination with horse pathogens has not been detected. Because only a small amount of blood is used as inoculum, and the Ehrlichiae can be passaged many times, costly separation of the *E. equi* or human granulocytic ehrlichia antigens from horse cells and contaminants can be avoided.

The vaccine and antigen preparations can also include promyelocyte cell antigens. Optionally, the vaccine and/or antigen preparations can be further purified from promyelocyte cell antigens by density gradient centrifugation or by antibody affinity purification using antibodies specific for Ep group Ehrlichiae and methods known to those of skill in the art.

Whole heat-killed *E. equi* or human granulocytic Ehrlichia agent, antigen preparations and/or nucleic acid preparations are combined with physiologically acceptable carriers to form vaccines. The physiologically acceptable carriers include buffered salt solutions, phosphate buffered saline, and cell culture medium. Optionally, the vaccine formulations can include adjuvants, such as alum, IPSCOMS, complete Freund's adjuvant, incomplete Freund's adjuvant, and saponin.

The vaccines are administered by a variety of routes including intravenous, intraperitoneal, intramuscular, intradermal and subcutaneous. The preferred route of administration is intramuscular. The vaccine can be administered in a single dose or multiple doses until a protective effect is achieved. It is preferred that the vaccine stimulate a protective immune response to infection with Ep group granulocytic Ehrlichia species. It is also preferred that the vaccine ameliorate and/or prevent the development of the symptoms of granulocytic ehrlichiosis.

Antigen preparations are also useful to prepare diagnostic tools, such as ELISA plates, latex agglutination, solid phase immunoassays, complement fixation tests and the like. Antigen preparations can be prepared from the Ep group granulocytic Ehrlichia species grown in mammalian cells that are likely to express antigens that react with antibodies produced after mammalian infection by using promyelocyte cultures, such as the HL60 or KG-1 cell lines as described below, and by standard methods.

In the preferred version for preparation of mammalian phase Ehrlichia species, *E. equi*- or HGE agent-infected peripheral blood or frozen infected promyelocyte cells are cultured with the HL60 or KG-1 cells in RMPI 1640 medium containing 10% (v/v) fetal bovine serum, 10 mM HEPES buffer, 2.0 mM L-glutamine in an environment of 5% $CO_2$ at 37° C. After about 10 days, morulae are detectable by Romanowsky staining, and by day 21, more than 50% of the HL60 cells contain Ehrlichia species morulae. The infected HL60 or KG-1 cells may then be harvested and used for antigen or nucleic acid preparation or as a source from which to purify Ep group granulocytic Ehrlichia species for vaccines.

Antigens for diagnostic serologic tests are preferably prepared by harvesting sufficient quantities of infected HL60 or KG-1 cells when approximately 50% or more of the cultured cells contain Ep group Ehrlichiae. The antigens may be used directly as fixed whole infected cells for indirect fluorescent antibody tests or may be purified by density-gradient centrifugation of lysed, infected tick cell cultures for latex agglutination, ELISA, solid phase enzyme immunoassay, or immunoblots. Nucleic acids derived from the Ehrlichiae cultured in HL60 and KG-1 cells may be used to prepare recombinant bacteriophage, viral, cosmid, phagemid, or plasmid genes that when transfected into appropriate hosts (bacteria, yeast, eukaryotic cells) will express recombinant Ep group ehrlichial proteins useful as vaccines or diagnostic reagents.

All publications and patent applications in this specification are indicative of the level of ordinary skill in the art to which this invention pertains. All publications and patent applications are herein incorporated by reference to the same extent as if each individual publication or patent application was specifically and individually indicated by reference.

The following examples are provided for illustrative purposes only and are in no way intended to limit the scope of the present invention.

EXAMPLE 1

Maintenance and Description of Human Promyelocytic Leukemia Cell Cultures

The HL60 and KG-1 human promyelocytic leukemia cell lines were derived from leukemia cells of human patients with promyelocytic leukemia. These cell lines and their maintenance are described in detail by the American Type Culture Collection, from which the cell lines are distributed (HL60- ATCC No. CCL 240 and KG-1- ATCC No. CCL 246). These cells have an immature granulocyte phenotype characteristic of promyelocytic bone marrow cells, but retain the ability to differentiate into more mature granulocytic cells or monocytic cells depending upon the conditions and supplements present in the cell culture medium.

The KG-1 cells are preferably cultured in suspension in a tissue culture medium, such as RPMI 1640 supplemented with 5.0 to 20% (v/v) heat-inactivated fetal bovine serum and 2.0 mM L-glutamine. Antibiotics, such as penicillin with streptomycin, or gentamicin may be added for maintenance cultures to suppress bacterial contamination, as is standard in the art. The doubling time of the cultures under these conditions is approximately 48 to 72 hr, and thus cell concentration must be carefully maintained, preferably below $1.0 \times 10^7$ cells per ml of tissue culture medium. Cell culture medium is preferably partially replaced 2 to 3 times per week with freshly prepared medium.

EXAMPLE 2

Infection of Human Promyelocytic Leukemia Cells with *Ehrlichia equi* or the Human Granulocytic Ehrlichia Derived from Infected Blood The HL60 (ATCC No. CCL 240) and KG-1 (ATCC No. CCL 246) human promyelocytic leukemia cell lines were propagated in RPMI 1640 medium with 10 to 20% (v/v) fetal bovine serum, 2.0 mM L-glutamine, with or without penicillin and streptomycin. Log phase HL60 or KG-1 cells were centrifuged, counted, and resuspended into fresh medium without penicillin and streptomycin at a cell density of $3.0 \times 10^6$ cells per ml. Whole ethylene diaminotetraacetic acid (EDTA) or acid citrate dextrose (ACD) anticoagulated human or equid blood known to be infected with the human granulocytic Ehrlichia or *E. equi*, of which less than 10% of human peripheral blood neutrophils contained Ehrlichia morulae and less than 50% of equid peripheral blood neutrophils contained *E. equi* or human granulocytic Ehrlichia morulae, were used. Between 300 to 500 l of this infected blood were added directly into 25 cm² plastic tissue culture flasks containing 5.0 to 9.0 ml of HL60 or KG-1 cells. Similarly, an equivalent inoculum of uninfected human or equid blood, or blood from a patient recovering from human granulocytic ehrlichiosis after 2 to 3 days of doxycycline therapy was incubated with 5.0 to 9.0 ml of HL60 or KG-1 cells, and 5.0 to 9.0 ml volumes of HL60 cells were held as uninoculated controls. The flasks were maintained in an atmosphere of 5% $CO_2$ at 37° C. Cell cultures were examined every two to four days by removing small aliquots and preparing cytocentrifuged slides that were then examined microscopically after Romanowsky (LeukoStat, Fisher Scientific, Pittsburgh, Pa.) staining. Aliquots of the same cells were stored for later examination to detect the presence of Ehrlichiae species and Ep group granulocytic Ehrlichiae DNA.

Before day 3, control HL60 and KG-1 cells, control HL60 and KG-1 cells inoculated with uninfected blood, blood from a doxycycline-treated patient recovering from human granulocytic ehrlichiosis, and HL60 cells inoculated with *E. equi*-infected equid blood appeared identical, except for the presence of occasional normal blood erythrocytes and leukocytes in the blood-inoculated cultures among the HL60 or KG-1 leukemia cells. By 3 days after inoculation, typical intracytoplasmic inclusions (morulae) filled with individual bacterial bodies (Ehrlichiae) were present within vacuoles of 3.0% of cells in the flask of KG-1 cells inoculated with human granulocytic Ehrlichia-infected equid blood. By 4 days after inoculation, typical intracytoplasmic inclusions (morulae) filled with individual bacterial bodies (Ehrlichiae) were present within vacuoles of 12.0% of cells in the flask of HL60 cells inoculated with *E. equi*-infected equid blood, and by 5 to 9 days after inoculation, typical intracytoplasmic inclusions (morulae) filled with individual bacterial bodies (Ehrlichiae) were present within vacuoles of 21.0 to 31.0% of cells in the flask of HL60 cells inoculated with human granulocytic Ehrlichia-infected human blood. No morulae were noted in any of the control HL60 or KG-1 flasks. Between 2 to 3 weeks after inoculation of cultures with infected blood, morulae were present in from 0 to 100% of cells, and in many cases, multiple, complex morulae in various stages from discrete organisms to large aggregates, and in some instances appearing to cause cell lysis and subsequent extracellular release of organisms. Control cells contained no such structures. The morphology of many of these morulae, especially in the early cultures, is quite similar to those seen in the peripheral blood neutrophils in human granulocytic ehrlichiosis in that these appeared to have generally even, rounded contours within the apparent cytoplasmic vacuoles.

The identity of the infecting bacterium was confirmed as Ep group granulocytic Ehrlichiae by the PCR and specific antibody reactions. The cultures were studied using primers designed based upon the 16S ribosomal RNA gene sequences ge9f (SEQ ID NO:1) and ge10r (SEQ ID NO:2). These primers amplify a 919 base pair product from *E. equi*, the human granulocytic Ehrlichia, and are predicted to amplify the same sequence from *E. phagocytophila*, and were used to assay for the presence of Ep genogroup DNA in the HL60 and KG-1 cell cultures inoculated with *E. equi*-infected and human granulocytic Ehrlichia-infected cells. Approximately 0.5 ml of cells ($5 \times 10^6$ cells) from this flask were added directly to DNA purification reagents of the PureGene DNA isolation kit (Gentra Systems, Minneapolis, Minn.), and the DNA was purified according to the manufacturer's instructions. Ehrlichia species DNA was amplified and detected in ethidium bromide stained agarose gels. Ep group DNA was not detected in control cultures at any time.

The infection of the HL60 and KG-1 cells was further confirmed by an indirect fluorescent antibody method using serum obtained from patient convalescent from HGE or from horses experimentally infected with *E. equi* or the human granulocytic Ehrlichia. The primary antibody source (patient anti-human granulocytic Ehrlichia serum, horse anti-*E. equi* or anti-human granulocytic Ehrlichia, and control human and horse sera) were used at a 1:80 dilution and reacted with *E. equi*- or human granulocytic Ehrlichia-infected HL60 or KG-1 cells followed by reaction with fluorescein conjugated anti-human immunoglobulins. The human anti-human granulocytic Ehrlichia sera and the horse anti-*E. equi* or anti-human granulocytic Ehrlichia sera, but not the control, fluoresced brightly in a pattern corresponding to the cytoplasmic structures clearly identifiable as morulae.

While the invention has been described in detail, and with reference to specific embodiments thereof, it will be apparent to one of ordinary skill in the art that various changes and modifications can be made therein without departing from the spirit and scope thereof.

We claim:

1. A method for culturing *Ehrlichia phagocytophila* genogroup of organisms in a cell culture comprising:

culturing a promyelocytic leukemia cell culture with *Ehrlichia phagocytophila* genogroup of organisms in a culture medium until growth of the *Ehrlichia phagocytophila* genogroup of organisms is detected, wherein the culture medium comprises a medium suitable for the growth of a promyelocytic leukemia cell culture.

2. The method of claim 1, wherein said promyelocytic leukemia cell culture is a culture of a member selected from the group consisting of HL60 cells, KG-1 cells, K-562 cells, HEL-92.1.7 cells, ML-1 cells, X-CGD PLB-985 cells, LAMA-84 cells, M-NF5-60 cells, WEHI-3 cells, and M1 cells.

3. An infected promyelocytic leukemia cell culture infected with *Ehrlichia phagocytophila* genogroup of organisms.

4. The infected promyelocytic leukemia cell culture of claim 3, wherein said cell culture is that of a member selected from the group consisting of HL60 cells, KG-1 cells, K-562 cells, HEL-92.1.7 cells, ML-1 cells, X-CGD PLB-985 cells, LAMA-84 cells, M-NF5-60 cells, WEHI-3 cells, and M1 cells.

5. The method of claim 1 wherein the culture is grown at a temperature of about 37° C.

* * * * *

UNITED STATES PATENT AND TRADEMARK OFFICE
CERTIFICATE OF CORRECTION

PATENT NO. : 5,955,359
DATED : September 21, 1999
INVENTOR(S) : J. Stephen Dumler, John Madigan, Jesse Goodman It is certified that error appears in the above-identified patent and that said Letters Patent is hereby corrected as shown below:

Column 1,
Lines 13-18 change "The work described herein was supported in part with funds from the Minnesota Agricultural Experiment Station (Project 377-3457), a Special Research Initiative Support Award from the University of Maryland School of Medicine, and Equine Research Laboratory Grant No. 95-01 from the University of California, Davis." to -- The work described herein was supported in part with funds from the Minnesota Agricultural Experiment Station (Project 377-3457), a Special Research Initiative Support Award from the University of Maryland School of Medicine, Equine Research Laboratory Grant No. 95-01 from the University of California, Davis, and the National Institutes of Health (Grant #AR37909). --

Signed and Sealed this

Seventh Day of August, 2001

*Attest:*

*Attesting Officer*

NICHOLAS P. GODICI
*Acting Director of the United States Patent and Trademark Office*

SEQUENCE LISTING

<160> NUMBER OF SEQ ID NOS: 4

<210> SEQ ID NO 1
<211> LENGTH: 25
<212> TYPE: DNA
<213> ORGANISM: synthetic construct

<400> SEQUENCE: 1
aacggattat tctttatagc ttgct                                              25

<210> SEQ ID NO 2
<211> LENGTH: 25
<212> TYPE: DNA
<213> ORGANISM: synthetic construct

<400> SEQUENCE: 2
ggagattaga tccttcttaa cggaa                                              25

<210> SEQ ID NO 3
<211> LENGTH: 28
<212> TYPE: DNA
<213> ORGANISM: synthetic construct

<400> SEQUENCE: 3
gtcgaacgga ttattcttta tagcttgc                                           28

<210> SEQ ID NO 4
<211> LENGTH: 28
<212> TYPE: DNA
<213> ORGANISM: synthetic construct

<400> SEQUENCE: 4
cccttccgtt aagaaggatc taatctcc                                           28